United States Patent [19]

Francis, Jr.

[11] Patent Number: 4,856,651
[45] Date of Patent: Aug. 15, 1989

[54] CHEMICAL THERMAL PACK AND METHOD OF MAKING SAME

[76] Inventor: Sam E. Francis, Jr., 5260 Lake Washington Rd., Melbourne, Fla. 32935

[21] Appl. No.: 136,621

[22] Filed: Dec. 22, 1987

[51] Int. Cl.⁴ .......................... A61F 7/00; B65D 81/32
[52] U.S. Cl. ............................................ 206/219; 62/4; 62/530; 126/263; 128/403
[58] Field of Search ............... 206/216, 219–222; 44/3.3, 3.6, 3.8; 62/4, 530; 126/263; 128/403

[56] References Cited

U.S. PATENT DOCUMENTS

| | | |
|---|---|---|
| 2,979,463 | 4/1961 | Ferguson . |
| 3,175,558 | 3/1965 | Callouette et al. ................. 128/403 |
| 3,301,250 | 1/1967 | Glasser ................................ 126/263 |
| 3,328,136 | 6/1967 | Verakas, Jr. . |
| 3,643,665 | 2/1972 | Caillouette et al. ............... 128/403 |
| 3,763,622 | 10/1973 | Stanley, Jr. . |
| 3,874,504 | 4/1975 | Verakas ............................... 206/219 |
| 3,893,834 | 7/1975 | Armstrong ............................ 62/4 |
| 3,906,926 | 9/1975 | Staples ................................ 126/263 |
| 3,951,127 | 4/1976 | Watson et al. ..................... 126/263 |
| 4,372,318 | 2/1983 | Viesturs et al. .................... 128/403 |
| 4,522,190 | 6/1985 | Kuhn et al. ........................ 126/263 |
| 4,576,169 | 3/1986 | Williams ........................... 128/403 |
| 4,596,250 | 6/1986 | Beisang, III et al. ............... 62/530 |

FOREIGN PATENT DOCUMENTS 0712457 6/1965 Canada .................. 383/94
2220951 11/1973 Fed. Rep. of Germany ...... 206/219

Primary Examiner—Jimmy G. Foster
Attorney, Agent, or Firm—Mason, Fenwick & Lawrence

[57] ABSTRACT

A thermal pack including an outer pouch having a pair of opposed faces arranged generally parallel to each other and defined by a single sheet of plastic film folded along a predetermined fold line. A second sheet of plastic film is disposed between the pair of opposed faces. A continuous weld line circumscribes the periphery of the faces, with the weld line bonding together the periphery of the faces and the periphery of the second sheet to define first and second volumes within the outer pouch. The second sheet provides a common wall between the first and second volumes. A heat transfer material is disposed in the first volume and an insulating layer is disposed in the second volume, substantially covering the second sheet.

26 Claims, 2 Drawing Sheets

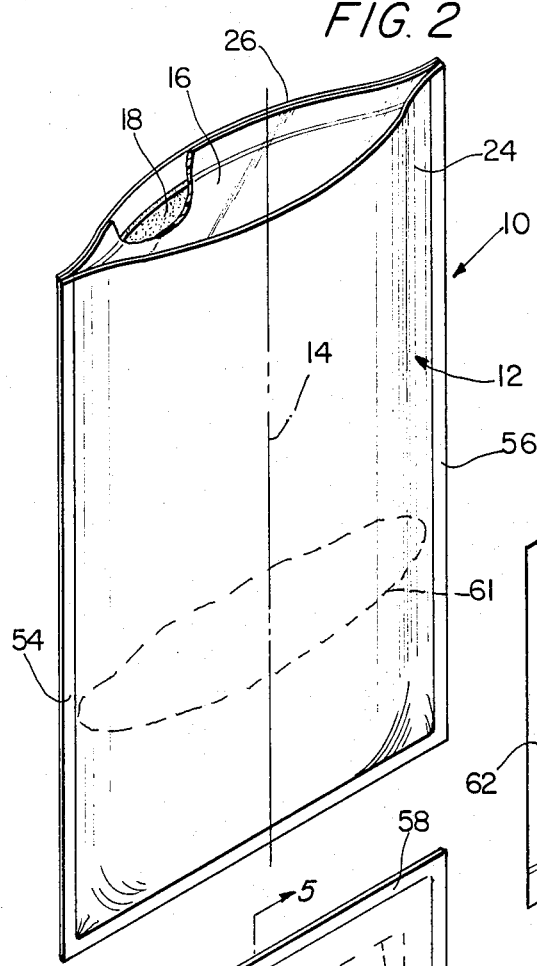
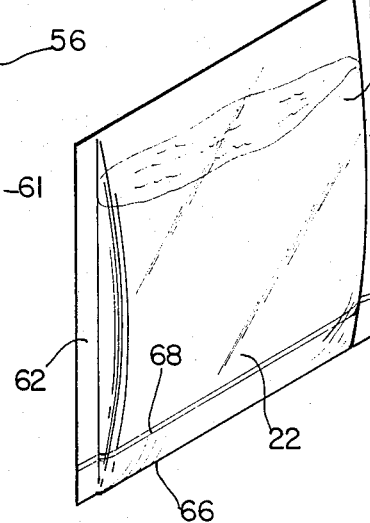
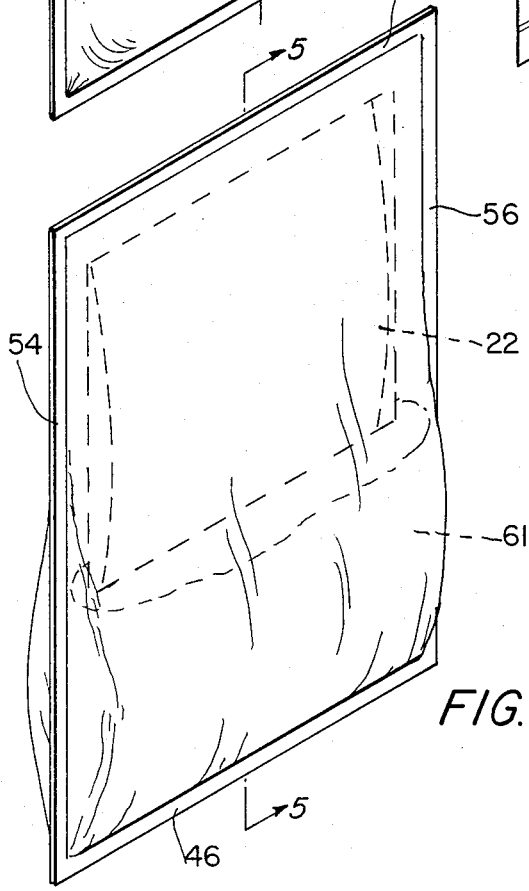
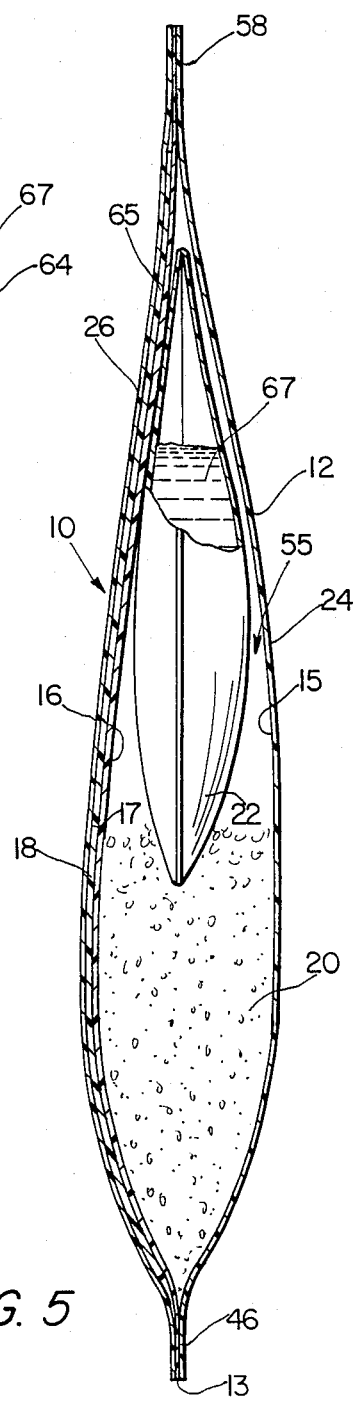

CHEMICAL THERMAL PACK AND METHOD OF MAKING SAME

BACKGROUND OF THE INVENTION

Various chemical thermal packs have been proposed heretofore which contain a suitable liquid solvent, principally water, and a quantity of particulate material that absorbs heat or produces heat when dissolved in that liquid. These ingredients may be packaged in a flexible sealed pouch, with the liquid solvent segregated from the powder by a membrane that ruptures when the pouch is manually squeezed. When the solvent and powder mix with each other, the powder either produces heat or absorbs heat, depending upon its composition.

One example of a heat-producing thermal pack is disclosed in U.S. Patent No. 3,328,136, as including a suitable heat-producing particulate material having magnesium sulfate as its principal constituent. The liquid solvent for such heat-producing particulate material preferably is at least 90% water, with a few drops of coloring and the remainder is an organic salt, such as sodium chloride or potassium chloride, to give the liquid solvent a lower freezing point. Alternatively, the hot pack may have calcium chloride as the principal ingredient of the heat-producing powder and water as the solvent.

As an example of a heat-absorbing thermal pack, a suitable heat-absorbing particulate material, as disclosed in U.S. Patent 2,979,463, may have as its principal ingredient urea or a urea compound, as a temperature depressant, along with the following:

One or more additional temperature depressants, such as ammonium chloride, potassium chloride or sodium chloride;

One or more heat-insulating substances, such as plaster of Paris or asbestos, to prolong the refrigerating effect;

One or more water absorbers, such as locust bean gum, and other minor constituents.

The liquid solvent for such heat-absorbing particulate material preferably is water with a few drops of coloring.

Alternatively, the cold pack may have ammonium nitrate as the principal ingredient of the heat-absorbing powder and water as the solvent.

A third type of thermal pack, known as a gel pack, can be placed in a hot or cold environment and will stay at a particular temperature when removed from that environment. Such a pack may contain water mixed with urea, potassium chloride and a gum such as locust bean gum. Alternatively, a water solution of calcium chloride may be used as the heat- or cold-sustaining mixture.

Such thermal packs have various uses, such as to warm the hands, or warm a baby bottle. The packs may also be used to warm, or cool an injured or painful part of the body, and in a great number of other situations that arise where promptly available, localizing heating or cooling effect for a limited period of time is desired.

Many such previous thermal packs were not entirely satisfactory from the standpoints of thermal efficiency and convenience of use because the heat transfer action takes place relatively freely at all exposed surfaces of the pack, with a resulting waste of the heating or cooling effect and often personal discomfort to the person holding the pack.

To overcome these deficiencies, it has been proposed heretofore to attach single-layer or multi-layer heat insulation to the outside or the inside of thermal packs. The arrangement with the insulation attached on the outside enables the interior of the thermal pack to be constructed substantially as before, but this tends to complicate and increase the cost of manufacture of thermal packs.

An example of a thermal pack with the insulation on the inside is U.S. Patent No. 3,874,504. This patent is directed to a chemical thermal pack which has a sealed intermediate envelope filled with the powder that produces or absorbs heat when dissolved in water and a quantity of water separated from the powder by a membrane that may be readily ruptured. A relatively flat, sealed, flexible outer pouch slidably receives the filled intermediate envelope and the heat insulation sheet that is located along the inside of one major face of the pouch to retard heat transfer there when the pouch is squeezed manually to rupture the membrane. The patent also discloses use of an insulated pack containing gel in place of the powder and water.

Although this pack has met with great success, there is still room for improvement especially as it relates to the more economical production of a chemical thermal pack as well as a pack with increased durability and simplicity of construction.

The present invention is directed toward filling those needs.

SUMMARY OF THE INVENTION

The present invention relates to a novel and improved thermal pack and a method of constructing the same. The thermal pack basically comprises a generally elongated outer pouch having a longitudinal axis. Preferably, the outer pouch is a flexible, transparent or opaque laminate material, such as biax nylon or mylar, and is relatively flat with its opposite major faces integrally joined to each other by side weld seams, a top weld seam and a bottom weld seam. Disposed within the pouch between the two outer faces or layers is a plastic film. Preferably, the transparent film is a flexible, laminate material that may be either transparent or opaque.

In a preferred embodiment, the transparent film is made from polyethylene plastic in 2 mil sheets. Positioned between the transparent film and the inner face of an outer layer of the pouch is a thermal insulation sheet. The thermal insulation sheet may be of a fine cell or cross-linked polyethylene or other suitable material. In a preferred embodiment, the insulation sheet is made from a 1/16" sheet of material trading under the name Jiffy Foam. Heat transfer powder and a liquid-containing rupturable bubble is positioned within the outer pouch in the area defined between the transparent film and the inner surface of the other face of the pouch. Such a construction provides a thermal pack which is heat insulated on one side. In an alternative embodiment of the subject invention, the heat transfer powder and rupturable bag are replaced by a permanent gel.

To make a thermal pack according to the teachings of the present invention, the outer pouch is formed from a single layer of plastic sheet material having a width defined between two side edges that is approximately twice the length of a finished pack as measured along the longitudinal axis of the thermal pack.

At a first work station, a continuous strip of insulated material is positioned between one side edge and the longitudinal axis of the continuous sheet. The insulated layer has a width which is narrower than the distance from the longitudinal axis and the edge of the sheet as measured in a direction generally perpendicular to the axis.

At another work station, a transparent sheet is placed in intimate contact with the insulation layer. The width of the transparent layer is equal to the distance from the longitudinal axis to the edge of the sheet measured in a direction perpendicular to the axis.

At an initial sealing station, the sheet is folded along the longitudinal axis so that the unoccupied portion of the sheet is folded on top of and placed into intimate contact with the transparent layer. After being folded, the plastic sheet is passed through a welding and sealing device where a welding operation is performed to provide a weld line along the bottom edge of a finished thermal pack. At the same time, another welding operation is performed to temporarily tack the outer layer to the transparent film along the top edge of the thermal pack.

The structure is then advanced to a second welding and sealing station where a heating apparatus creates two double width vertical welds. The structure then advances to a cutting station where the vertical welds are divided in half to provide two side weld lines one on each side of a pair of finished thermal packs.

At the next station, the sides of the bag are subjected to suction forces in order to draw open the top of the bag to reveal the volume created between one side of the transparent film and the interior of one of the faces. After the suction has been applied to open the top of the bag, a portion of the heat transfer powder is introduced inside the pouch. At the next station, a rupturable bag pre-filled with liquid is inserted inside the pouch but above the heat transfer powder. After this, the top of the bag passes through another welding station where a top weld is created.

BRIEF DESCRIPTION OF THE DRAWINGS

FIG. 2 is a perspective view of a partially completed thermal pack filled with a portion of permanent gel and embodying the teachings of the present invention.

FIG. 3 is a perspective view of a liquid-containing rupturable bubble for use in a preferred embodiment of the subject invention.

FIG. 4 is a perspective view of an alternative embodiment of the thermal pack.

FIG. 5 is a view taken along lines 5—5 of FIG. 4.

DETAILED DESCRIPTION OF THE PREFERRED EMBODIMENTS

Figure 1:
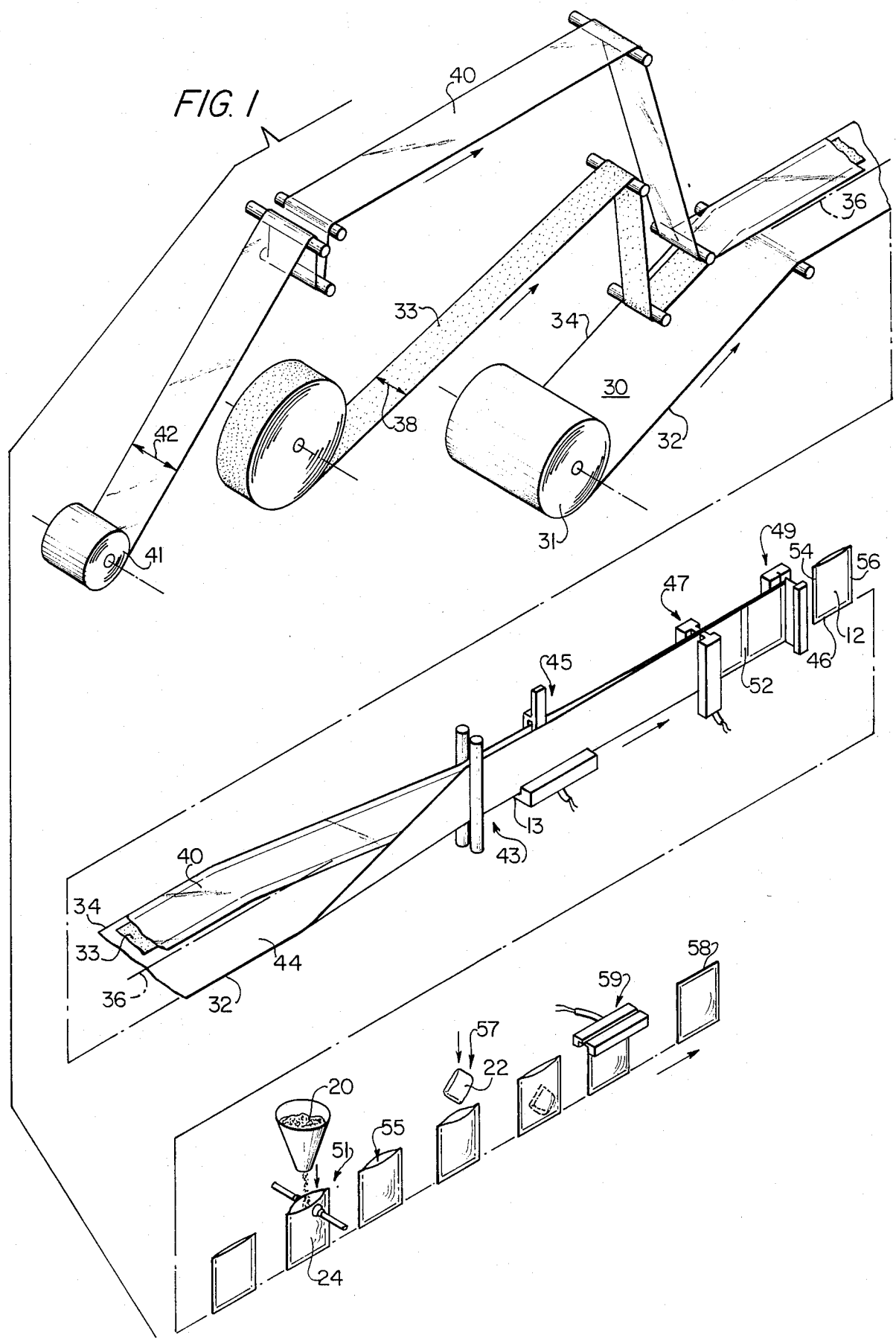
FIG. 1 is a diagrammatic representation of a preferred embodiment of a method for making a novel and improved thermal pack.

In describing the preferred embodiments of the subject invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The present invention relates to a novel and improved thermal pack and a method of constructing the same. FIGS. 2 to 5 generally disclose the thermal pack produced according to the teachings of the present invention. The thermal pack 10 basically comprises a generally elongated outer pouch 12 having a longitudinal axis 14. Preferably, the outer pouch is a flexible, laminate material or a transparent or opaque laminate material such as biax nylon or mylar, and is relatively flat with its opposite major faces 24 and 26 integrally joined to each other by side weld seams 54 and 56, top weld seam 58 and bottom weld seam 46. Disposed within the pouch between the two outer layers of the pouch is a transparent film 16. Positioned between the transparent film 16 and an inner surface 17 of outer layer 26 of the pouch is a thermal insulation sheet 18. The thermal insulation sheet may be of a fine cell or crosslinked polyethylene or other suitable material. In a preferred embodiment, the insulation sheet is made from a 1/16" sheet of material trading under the name Jiffy Foam. Heat transfer powder 20 and a liquid-containing rupturable bubble 22 is positioned within the outer pouch in the area defined between the transparent film 16 and the outer face 24 of pouch 12. Such a construction provides a thermal pack which is heat insulated on one side.

In an alternative embodiment of the subject invention, the heat transfer powder 20 and rupturable bag 22 are replaced by a permanent gel.

With reference to FIGS. 1 to 5, a preferred embodiment of the method for making thermal packs according to the teachings of the present invention will now be described in greater detail. The outer pouch 12 is formed from a single layer of plastic sheet material 30 having a width defined between two side edges 32 and 34 that is approximately twice the length of a finished pack as measured along the longitudinal axis 14 of the thermal pack. During manufacture, the sheet is continuously fed from a supply roll 31.

At a first work station, a continuous strip of insulated material 33 is fed from a supply roll and positioned between side edge 34 and longitudinal axis 36 of continuous sheet 30 so that one face of the insulated sheet is in intimate contact with the plastic sheet 30. Insulated sheet 33 has a width 38 which is narrower than the distance from the longitudinal axis 36 and the edge 34 of the sheet 30 as measured in a direction generally perpendicular to the axis 36.

At another work station, a transparent sheet 40 is fed from a supply roll 41 and placed in intimate contact with the insulation layer 33. The width 42 of the transparent layer 40 is equal to the distance from the longitudinal axis 36 to the edge 34 of the sheet 30 measured in a direction perpendicular to the axis 36.

At an initial sealing station 43, the sheet 30 is folded along the longitudinal axis 36 so that the unoccupied portion 44 of sheet 30 is folded on top of and placed into intimate contact with the transparent layer 40. After being folded, the plastic sheet 30 is passed through a welding and sealing device 45 where a welding operation is performed to provide a weld line 46 along what will eventually become the bottom edge 17 of a finished thermal pack. At the same time, another welding operation is performed to temporarily tack the outer layer 26 to the transparent film 40 along what will eventually become the top edge 15 of the finished thermal pack.

As can be seen in FIG. 5, weld line 46 includes the welding of the two outer faces 24 and 26 to the transparent layer 16 throughout the entire length of the horizontal weld line. The weld line 46 is created without destroying the integrity of the fold 13 formed when plastic sheet 30 is folded along longitudinal axis 36.

The structure is then advanced to a second welding and sealing station 47 where a heating apparatus creates double width vertical welds 52. The structure then advances to a cutting station 49 where the vertical welds 52 are divided in half to provide two side weld lines 54 and 56, one on each side of a pair of finished thermal packs. The side welds are created in such a way that they merge into bottom weld line 46.

At the next station 51, the sides of the bag are subjected to suction forces in order to draw open the top of the bag to reveal the volume 55 between one side of the plastic insert and the interior of face 24. After the suction has been applied to open the top of the bag, a portion of the heat transfer powder 20 is introduced inside the pouch. At the next station 57, a rupturable bag 22 prefilled with liquid is inserted inside the pouch but above the heat transfer powder. After this, the top of the bag passes through another welding station 59 where a top weld 58 is created. In this way, the entire interior of the resulting thermal pack is surrounded by a continuous weld formed along the peripheral edge of the pack by bottom weld 46, side weld 54, top weld 58 and side weld 56. At the same time, it is to be understood that the sheet of transparent film 16 has also been welded on all side edges about its periphery between the outer layers 24 and 26 of the pouch defined along the weld lines. The result is a pouch divided into volumes which are separated from each other. Each of the volumes is defined by one of the outer layers 24 and 26 of pouch 12. The two volumes share in common a wall created by the transparent film 16. As stated before, one of the volumes 55 contains the heat transfer powder and the rupturable bag. In an alternative embodiment of the invention, the heat transfer powder and the bag are replaced by a permanent gel 61 (shown in phantom in FIG. 2).

The other volume 65 of the pouch houses the insulated layer 18. As shown in FIGS. 2 and 5, the sheet of insulated material 18 is secured along the two side welds 54 and 56 but not along either the top weld 58 or the bottom weld 46.

With reference to FIGS. 3 and 5, the rupturable bag 22 is made from a continuous sleeve of material sealed at both ends 62, 64. A quantity of liquid 67 fills the bag. Preferably the liquid is water. In a preferred embodiment, the rupturable bag is generally a rectangular configuration when empty. Along one of the sides 66 that is generally perpendicular to the seals 62 and 64, there is disposed a perforated strip 68. This strip is defined in such a way that it does not permit liquid to vacate the bag under normal circumstances; instead it provides a weak point to facilitate rupturing the bag to release the liquid to mix with the heat transfer powder 20 within the pouch 12.

From the above, it is apparent that many modifications and variations of the present invention are possible in light of the above teachings. It is, therefore, to be understood that, within the scope of the appended claims, the invention may be practiced otherwise than as specifically described.

What is claimed is:

1. A thermal pack comprising:
   an outer pouch having a pair of opposed faces arranged generally parallel to each other and defined by a single sheet of flexible plastic film folded along a predetermined fold line;
   a second sheet of flexible plastic film disposed between said pair of opposed faces;
   a continuous weld line circumscribing and sealing the periphery of said faces, said weld line bonding together the periphery of said faces and the periphery of said second sheet so that said second sheet and said opposed faces define first and second volumes within said outer pouch, said second sheet providing a common wall between said first and second volumes;
   a heat transfer material disposed in said first volume; and
   an insulating layer disposed in said second volume and substantially covering said second sheet.

2. The thermal pack according to claim 1, wherein said insulating layer is at least partially bonded within said continuous weld line.

3. The thermal pack according to claim 1, wherein each of said opposed faces is shaped like an elongated rectangle having a longitudinal axis, said continuous weld line being defined by two side welds disposed generally parallel to said longitudinal axis, a bottom weld disposed generally perpendicular to said longitudinal axis and a top weld disposed generally perpendicular to said longitudinal axis.

4. The thermal pack according to claim 3, wherein said fold line is disposed along said bottom weld line.

5. The thermal pack according to claim 3, wherein said insulating layer is bonded within said two side welds.

6. The thermal pack according to claim 1, wherein said heat transfer material is a permanent gel.

7. The thermal pack according to claim 1, wherein said heat transfer material comprises a heat transfer powder and a liquid-containing rupturable bubble.

8. The thermal pack according to claim 1, wherein said single sheet of plastic material is a laminate material.

9. The thermal pack according to claim 8, wherein said second sheet of plastic film is a laminate material.

10. The thermal pack according to claim 1, wherein an ingredient of said heat transfer material is water.

11. A thermal pack comprising:
    an outer pouch having a pair of opposed faces arranged generally parallel to each other and defined by a single sheet of flexible plastic film folded along a predetermined fold line, each of said opposed faces being shaped like an elongated rectangle having a longitudinal axis;
    a second sheet of flexible plastic film disposed between said pair of opposed faces;
    a continuous weld line circumscribing and sealing the periphery of said faces, said weld line bonding together the periphery of said faces and the periphery of said second sheet so that said second sheet and said opposed faces define first and second volumes within said outer pouch, said second sheet providing a common wall between said first and second volumes, said weld line being defined by two side welds disposed generally parallel to said longitudinal axis, a bottom weld disposed generally perpendicular to said longitudinal axis and a top weld disposed generally perpendicular to said longitudinal axis;
    a heat transfer material disposed in said first volume; and
    an insulating layer disposed in said second volume and substantially covering said second sheet, said insulating layer being bonded within said two side welds.

12. The thermal pack according to claim 11, wherein said insulating layer is at least partially bonded within said continuous weld line.

13. The thermal pack according to claim 11, wherein said fold line is disposed along said bottom weld line.

14. The thermal pack according to claim 11, wherein said heat transfer material is a permanent gel.

15. The thermal pack according to claim 11, wherein said heat transfer material comprises a heat transfer powder and a liquid-containing rupturable bubble.

16. The thermal pack according to claim 11, wherein said single sheet of plastic material is a laminate material.

17. The thermal pack according to claim 11, wherein said second sheet of plastic film is a laminate material.

18. The thermal pack according to claim 11, wherein an ingredient of said heat transfer material is water.

19. A thermal pack comprising:
- an outer pouch having a pair of opposed faces arranged generally parallel to each other and defined by a single sheet of flexible plastic film folded along a predetermined fold line;
- a continuous weld line circumscribing and sealing the periphery of said faces, said weld line bonding together the periphery of said faces to define a first sealed volume;
- a second sheet means disposed within said first sealed volume, said second sheet means being sealed between said faces along at least a portion of said continuous weld line to define a second sealed volume;
- a heat transfer material disposed in said second volume; and
- an insulating layer disposed in said first volume and sized to substantially conform to the size of one of said opposed faces.

20. A thermal pack comprising:
- an outer pouch having a pair of opposed faces arranged generally parallel to each other and defined by a single sheet of flexible plastic film folded along a predetermined fold line, each of said opposed faces being shaped like an elongated rectangle having a longitudinal axis;
- a continuous weld line circumscribing and sealing the periphery of said faces, said weld line bonding together the periphery of said faces to define a first sealed volume;
- a second sheet disposed within said first sealed volume, said second sheet means being sealed between said faces along at least a portion of said continuous weld line to define a second sealed volume, said weld line being defined by at least two side welds disposed generally parallel to said longitudinal axis, and a top weld disposed generally perpendicular to said longitudinal axis;
- a heat transfer material disposed in said second volume; and
- an insulating layer disposed in said first volume and sized to substantially conform to the size of one of said opposed faces.

21. The thermal pack according to claim 20, wherein said insulating layer is at least partially bonded within said continuous weld line.

22. The thermal pack according to claim 20, wherein said heat transfer material is a permanent gel.

23. The thermal pack according to claim 20, wherein said heat transfer material comprises a heat transfer powder and a liquid-containing rupturable bubble.

24. The thermal pack according to claim 20, wherein said single sheet of plastic material is a laminate material.

25. The thermal pack according to claim 20, wherein said second sheet of plastic film is a laminate material.

26. The thermal pack according to claim 20, wherein an ingredient of said heat transfer is water.

* * * * *